United States Patent [19]

Takahashi et al.

[11] Patent Number: 5,702,905
[45] Date of Patent: Dec. 30, 1997

[54] MONOCLONAL ANTIBODY TO HUMAN VENTRICULAR MYOSIN LIGHT CHAINS

[75] Inventors: Miyoko Takahashi, North York; George Jackowski, Inglewood, both of Canada

[73] Assignee: Spectral Diagnostics, Toronto, Canada

[21] Appl. No.: 314,202

[22] Filed: Sep. 28, 1994

[51] Int. Cl.$^6$ .................................................. G01N 33/53
[52] U.S. Cl. ...................... 435/7.1; 435/7.92; 435/70.21; 435/331; 436/518; 530/387.9; 530/388.1
[58] Field of Search .......................... 435/7.1, 7.92, 435/7.93, 7.94, 7.95, 70.21, 240.27, 331; 436/518, 548; 530/387.9, 388.1

[56] References Cited

U.S. PATENT DOCUMENTS 4,879,216  11/1989  Hallermayer et al. .

FOREIGN PATENT DOCUMENTS 1289870  10/1991  Canada .
9015993  12/1990  WIPO .
WO 90/15329  12/1990  WIPO .

OTHER PUBLICATIONS

Bhayana et al. (1994) Clin. Chem. 40:1027.
Jackowski et al. (1994) Clin. Chem. 40:1031.
Katoh et al. (1992) Clin. Chem. 38:170–1.
Hoffmann et al. (1988) Nuc. Acids Rrs. 16:2353.
Nicol et al., 1993, J. Nucl. Med. 34:2144–51.
Katoh et al., 1991, Clin. Chem. 37:1030 (abstract #0572).
Uji et al., 1991, J. Clin. Lab. Anal. 5:242–46.
Hirayama et al., 1990, Clin. Biochem. 23:515–22.
Looser et al., 1988, Clin. Chem. 34:1273 (abstract #589).
Katus et al., 1983, Abstracts Circulation 68 (Suppl. III):80 (abstract #320).
Scheffold et al., 1983, Eur. Heart J. 4 (Suppl. E):87 (abstract #11).
Haber et al., 1982, J. Mol. Cell. Cardiology 14 (Suppl. 3):139–46.
Katus et al., 1982, Mol. Immunol. 19:451–55.
Katus et al., 1980, Abstracts Circulation 62 (Suppl. III):216 (abstract #824).

*Primary Examiner*—Marianne P. Allen
*Assistant Examiner*—Patricia A. Duffy
*Attorney, Agent, or Firm*—Klauber & Jackson

[57] ABSTRACT

A monoclonal antibody having high affinity to the cardiac isoform of human myosin light chains is described. The monoclonal antibody is prepared against a synthetic peptide from the amino terminal end of myosin light chain-1. The monoclonal antibody can be used as a reagent in an immunoassay system to identify blood, serum or plasma levels of myosin light chains. Such an immunoassay system can be used for diagnosing and quantifying myocardial necrosis and infarction.

3 Claims, 2 Drawing Sheets

MONOCLONAL ANTIBODY TO HUMAN VENTRICULAR MYOSIN LIGHT CHAINS

FIELD OF INVENTION

This invention relates to a monoclonal antibody which demonstrates specific binding to human myosin light chains and high affinity to the cardiac isoform of these same light chains. More specifically, this invention relates to the hybridoma cell line, designated as 39-15 (ATCC HB 11709), and the monoclonal antibody produced by the same. The monoclonal antibody of the present invention can be used for determining blood, serum or plasma levels of cardiac myosin light chains. The antibody is particulary useful for rapid format diagnostic tests for cardiac muscle damage.

BACKGROUND AND PRIOR ART

Myosin is a large and insoluble structural protein of the sarcomere. However, some cytosolic precursor pool of the light chains seem to exist in the muscle cells. Such cytosolic pool will readily leak out into circulation following myocardial damage. In addition, MLCs appear to dissociate from the whole myosin complex if the cellular pH drops below 6.0 (T. C. Smitherman, et al., J Mol Cell Cardiol, 12, 149–164, 1980). Muscle cell damage, may release the dissociated MLCs into circulation. Thus the detection of MLCs in circulation has been proposed as a biochemical marker of myocardial damage.

Myosin molecules, found in both cardiac and skeletal muscle, are composed of pairs of light chains (MLC-1 with a molecular weight of 27 Kd and MLC-2 with a molecular weight of 20 Kd). Skeletal and cardiac MLCs are chemically and immunologically distinct despite their high homology (A. G. Weeds, et al., Nature 234, 85–88, 1971: T. Masaki, J Biochem, 76, 441–449, 1974). The carboxyl terminal ends of both MLC-1 and MLC-2 appear highly conserved whereas cardiac or skeletal specific sequences are found in the amino terminal end (E. Hoffmann, et al., Nucleic Acids Res, 16, 2353, 1988).

In recent years, there has been an increasing interest in human ventricular myosin light chains (HVMLCs) as a new biochemical marker of myocardial damage. Myosin light chains appear in the serum rapidly, and their levels remain elevated for up to 10 days following myocardial necrosis (J. Wang, et al., Clin Chimica, Acta, 181, 325–336, 1989; G. Jackowski, et al., Circulation Suppl, 11, 355, 1989). Measurement of HVMLC appear to offer diagnostic information on unstable angina and acute myocardial infarction.

Various immunological assays have been established to measure MLCs in human serum. Initial studies were performed with radioimmunoassays using polyclonal antibodies (J. B. Gere, et al., Am J Clin Pathol, 71, 309–318, 1979: H. A. Katus, et al., Am J Cardiol, 54, 964–970, 1984: M. Isobe, et al., Circulation, 76, 1251–1261, 1987: J. Wang, et al., Clin Chim Acta, 181, 325–336, 1989: H. A. Katus, et al., Mol Immunol, 19, 451–455, 1982). Using polyclonal antibodies, it was difficult to differentiate between cardiac and skeletal isoforms of MLCs. Due to significant homology between cardiac and skeletal isoforms, cross-reactivity problems were inevitable.

Attempts were made to overcome these problems by using monoclonal antibodies which recognize epitopes on MLC molecules (S. Looser, et al., Clin Chem, 34, 1273, 1988: Y. Uji, et al., J Clin Lab Anal, 5, 242–246, 1991: H. Katoh, et al., Clin Chem, 37, 1030, 1991: A. Hirayama, et al., Clin Biochem, 23, 515–522, 1990). These monoclonal antibodies were raised against human ventricular myosin light chains (HVMLCs) purified from cardiac tissue. Cross reactivity with skeletal MLC of such monoclonal antibodies were reported to be greater than 10%.

Recently, Nicol, P. D., et al. (J Nucl Med, 34, 2144–2151, 1993) used a synthetic peptide (residues 5–14 of HVMLC-1) which was coupled to keyhole limpet hemocyanin (KLH) as an immunogen to produce monoclonal antibodies. The affinity of this monoclonal antibody however, is not high enough for the present purpose.

There remains a need for a human myosin light chain monoclonal antibody that manifests high affinity for cardiac myosin light chains. Such an immunoassay system can be used for diagnosing and quantifying myocardial necrosis and infarction according to the rapid format procedure disclosed in U.S. Pat. No. 5,290,678.

SUMMARY OF THE INVENTION

The limitations of the prior art are addressed in the present invention by providing a monoclonal antibody that is specific for the myosin light chains and has high affinity for the cardiac isoforms. Specifically, the present invention relates to a monoclonal antibody produced against a cardiac specific synthetic peptide of MLC-1.

According to one embodiment of the present invention the synthetic peptide corresponds to residues 34 to 44 of HVMLC-1. This peptide was used, without any carrier proteins such as KLH or albumin, for the preparation of the monoclonal antibody of the invention.

According to the present invention there is further provided a monoclonal antibody, which recognizes not only the synthetic peptide described above, but also recognizes and has high affinity for cardiac myosin light chain in the blood, serum or plasma of patients with cardiac muscle damage (e.g. myocardial infarction, unstable angina).

According to one embodiment of this invention, there is provided the hybridoma cell line 39-15, deposited with American Type Culture Collection Rockville, Md. 20852 on Aug. 25, 1994 under Accession Number HB 11709. The monoclonal antibody produced from this hybridoma recognizes an epitope present within the amino acid residues 34–44 of the native HVMLC-1 molecule.

According to a further embodiment of the present invention, there is provided a method of detecting cardiac myosin light chain in a sample using a monoclonal antibody produced from hybridoma cell line 39-15, deposited with American Type Culture Collection under Accession Number HB 11709, which comprises contacting the sample with the monoclonal antibody to effect an immunoreaction between the cardiac myosin light chain in the sample and the monoclonal antibody; and detecting the immunoreaction.

DETAILED DESCRIPTION OF THE INVENTION

Figure 1:
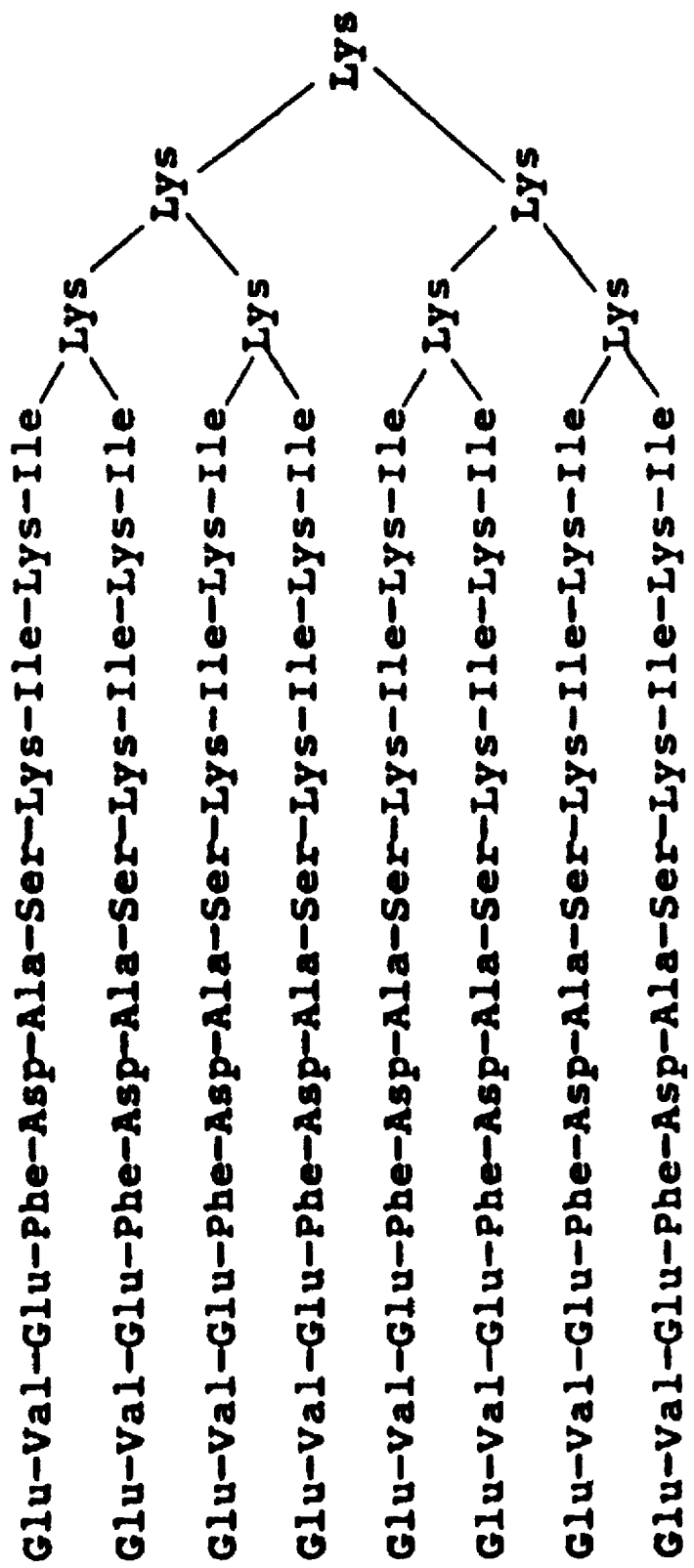
FIG. 1 shows the octameric structure of the peptide sequence of B39 (SEQ ID NO.: 1), with the branching polylysine core.

The monoclonal antibody of the present invention can be distinguished from the antibodies known in the art in that it is characterized for its diagnostic value due to its specificity and sensitivity for myosin light chain and its high affinity for cardiac myosin light chin.

As disclosed by E. Hoffman et al., (Nucleic Acid Res. 16, 2353, 1988), the carboxyl terminal end of both myosin light chain-1 and myosin light chain-2 appear highly conserved, whereas cardiac or skeletal specific sequences are found in the amino terminal end of the myosin light chains. Thus, a monoclonal antibody with high affinity for the cardiac isoform of myosin light chain was prepared according to the present invention using a synthetic peptide from the amino terminal end of the myosin light chain-1, spanning from position 34 to 44 of the myosin light chain-1.

Methods for preparing synthetic peptides are well known in the art and have been described in detail in the following references (C. Y. Wang et al., Science 254, 285–288, 1991; G. W. McLean et al., Journal of Immunological Methods, 137, 149–157, 1991 or P. D. Nicol et al., The Journal of Nuclear Medicine, 34, 2144–2151, 1993).

A single peptide chain is usually not very immunogenic in experimental animals, and it is generally necessary to couple the peptide to a carrier protein such as KLH or bovine serum albumin. However, antisera produced using protein-conjugated peptides are often low in titre. An approach to produce antisera against synthetic peptides has been described by D. N. Posnett et al. (J. Biol. Chem. 263, 1719, 1988); J. P. Tam (Proc. Natl. Acad. Sci., U.S.A., 85, 5409, 1988); and G. W. McLean, et al. (J. Immunol. Methods, 137, 149, 1991). The α and ε amino groups on lysine were used to synthesize a multiple branching poly-lysine core onto which the peptide of interest was synthesized. Using the branched peptides, they have demonstrated production of high titre antisera.

The monoclonal antibody of the present invention was prepared by conventional procedures, generally following the methods of Kohlers and Milstein (Nature, 256, 495–497, 1975; Eur. J. Immunol. 6, 511–519, 1976). According to this method, tissue culture adapted mouse myeloma cells are fused to antibody producing cells from immunized mice to obtain hybrid cells that produce large amounts of a single antibody molecule. In general, the antibody producing cells are prepared by immunizing an animal, for example, mouse, rat, rabbit, sheep, horse, or bovine, with an antigen. The immunization schedule and the concentration of the antigen in suspension is such as to provide useful quantities of suitably primed antibody producing cells. These antibody producing cells can be either spleen cells, thymocytes, lymph node cells and/or peripheral blood lymphocytes.

The antibody producing cells are then fused with myeloma cells, cell lines originating from various animals such as mice, rats, rabbits, and humans can be used, using a suitable fusion promoter. Many mouse myeloma cell lines are known and available generally from members of the academic community and various depositories, such as the American Type Culture Collection, Rockville, Md. The myeloma cell line used should be HAT sensitive so that unfused myeloma cells will not survive in a selective media, while hybrids will survive. The cell line most commonly used is an 8-azaguanine resistant cell line, which lacks the enzyme hypoxanthine-guanine- phosphoribosyl-transferase and therefore will not be supported by HAT (hypoxanthine-aminopterin-thymidine) medium. In general, the cell line is also preferably a "non-secretor" type, in that it does not produce any antibody. The preferred fusion promoter is polyethyleneglycol having an average molecular weight from about 1000 to about 4000. Other fusion promoters such as polyvinylalcohol, a virus or an electrical field can also be used.

The immortalized cells (hybridoma) must then be screened for those which secrete antibody of the correct specificity. The initial screening is generally carried out using an enzyme-linked immunosorbent assay (ELISA). Specifically, the hybridoma culture supernatants are added to microtitre plates which have been previously coated with the antigen, in this case either the branched peptide or myosin light chain purified from human cardiac muscle. A bound specific antibody from the culture supernatants can be detected using a labelled second antibody, for example, goat antimouse IgG labelled with peroxidase, which is commercially available. Cultures that are positive against both the peptide antigen and the myosin light chain antigen are then subjected to cloning by the limiting dilution method. Secondary hybridoma cultures are re-screened as described above, and further positive cultures are then examined using the BIAcore system (Pharmacia Biosensor AB, Uppsala, Sweden). The cultures are then evaluated as to determine whether or not the antibody binds the antigen and to determine the kinetic profile of antigen binding. Selected cultures based on these results are subject to further cloning until culture stability and clonality are obtained. Immediately after hybridization, the fusion products will have approximately 80 chromosomes, and as these cells proceed to divide they will randomly lose some of these chromosomes. The cloning process is to select those cells which still have the chromosomes coding for antibody production. The cloning process is repeated until 100% of the sub-population exhibits the production of a specific antibody, which is indicative of the "stability" of the hybridoma. In addition, hybridoma culture wells often have multiple colonies some of which may be antibody non-producers. The cloning process allows the selection of a positive hybrid which is derived from a single cell.

The monoclonal antibody of the present invention can be produced either using a bioreactor or from ascites, both procedures of which are well known in the art.

The monoclonal antibody of the present invention can be used in an immunoassay system for determining blood, serum or plasma levels of myosin light chain.

Current immunoassays utilize a double antibody method for detecting the presence of an analyte. These techniques are reviewed in "Basic Principals of Antigen-Antibody Reaction", Elvin A. Labat, (Methods in Enzymology, 70, 3–70, 1980). Such systems are often referred to as fast format systems because they are adapted to rapid determinations of the presence of an analyte. The system requires high affinity between the antibody and the analyte. According to one embodiment of the present invention, the presence of myosin light chain is determined using a pair of antibodies, each specific for myosin light chain. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting myosin light chain in a sample of biological fluid. In this method, the analyte (myosin light chain) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports were plates, tubes or beads of polystyrene which are well known in the field of radioimmunoassay and enzyme immunoassay. More recently, a number of porous material such as nylon, nitrocellulose, cellulose acetate, glass fibres and other porous polymers have been employed as solid supports.

One embodiment of the present invention uses a flow-through type immunoassay device. Valkirs et al. (U.S. Pat. No. 4,632,901) discloses a device comprising antibody, specific to an antigen analyte, bound to a porous membrane or filter to which is added a liquid sample. As the liquid flows through the membrane, target analytes bind to the antibody. The addition of the sample is followed by the addition of a labelled antibody. The visual detection of the labelled antibody provides an indication of the presence of the target analyte in the sample.

Another example of a flow-through device is disclosed in Kromer et al. (EP-A 0 229 359), which described a reagent delivery system comprising a matrix saturated with a reagent or components thereof dispersed in a water soluble polymer for controlling the dissolution rate of the reagent for delivery to a reaction matrix positioned below the matrix.

In migration type assays, a membrane is impregnated with the reagents needed to perform the assay. An analyte detection zone is provided in which labelled analyte is bound and assay indicia is read. For example, see Tom et al. (U.S. Pat. No. 4,366,241), and Zuk (EP-A 0 143 574). Migration assay devices usually incorporate within them reagents which have been attached to coloured labels thereby permitting visible detection of the assay results without addition of further substances. See for example Bernstein (U.S. Pat. No. 4,770,853), May et al. (WO 88/08534), and Ching et al. (EP-A 0 299 428). The monoclonal antibody of the present invention can be used in all of these known types of flow through devices.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of coloured labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70, 419–439, 1980 and in U.S. Pat. No. 4,857,453.

Other examples of biological diagnostic devices, which can be used for the detection of myosin light chain, using the monoclonal antibody of the present invention, include the devices described by G. Grenner, P. B. Diagnostics Systems, Inc., in U.S. Pat. Nos. 4,906,439 and 4,918,025.

In one embodiment of the present invention, the diagnostic test uses a blood sample tube which is commonly used to draw blood samples from patients. The inside wall of the tube acts as a carrier for the monoclonal or polyclonal antibodies and required reagents or detection means, needed to produce a measurable signal. In this embodiment the capture antibody is immobilized onto the wall of the test tube. After the sample is drawn from the patient, the user simply shakes the sample with the detector antibody in the tube so that the detector antibody reacts with any myosin light chain in the blood. In this example the monoclonal antibody of the present invention can be either the capture antibody or the detector antibody. It may be necessary to use a sample wherein the red blood cells have been removed, so that the red blood cells will not interfere with the analysis of the results. If the analyte is present in the blood, it will be sandwiched between the capture antibody and the detector antibody which contains a suitable label for direct detection or reacts with the reagents in the reagents in an indirect assay. The solid support (the test tube) can then be rinsed free of unbound labelled material. A variety of solid supports can be used according to this method, for example, test tube walls, plastic cups, beads, plastic balls and cylinders including microtitre plates, paper, and glass fibres.

There are currently available several types of automated assay apparatus which can undertake rapid format assays on a number of samples contemporaneously. These automated assay apparatus include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of work stations each of which performs one of the steps in the test procedure. The assay element may be transported from one work station to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a colorimetric change in the reagents present on the porous member to be read, such as by a means of a spectroscopy or fluorometer which are included within the assay system.

The automated assay instruments of PB Diagnostic Systems, Inc. are described in U.S. Pat. Nos. 5,051,237; 5,138,868; 5,141,871 and 5,147,609.

A description of the IMX Analyzer is included in the "Abbott IMX Automated Bench Top Immunochemistry Analyzer System" by Fiore, M. et al., *Clinical Chemistry*, 35, No. 9, 1988. A further example of these analyzers has been described in U.S. Pat. No. 4,956,148 entitled "Locking Rack and Disposable Sample Cartridge" issued to C. J. Grandone on Sep. 1, 1990, and assigned to Abbott Laboratories, which describes a carousel for carrying a plurality of reaction cells for use in connection with the Abbott IMX™ system. A further development in the art has been described in Canadian Patent Application 2,069,531, Chadwick M. Dunn et al., assigned to Abbott Laboratories wherein the immunochemistry analyzer system, described in this prior art application, has the capability of testing for up to three or four analytes in a single batch during a single run using currently available instrumentation. The system described in the Canadian application referred to above enables the users to group three small batches of assays together rather than run three separate analysis. The monoclonal antibody of the present invention can be used in these automated analyzers.

A further class of immunochemical analyzer systems, in which the monoclonal antibody of the present invention can be used, are the biosensors or optical immunosensor systems. In general an optical biosensor is a device which uses optical principles quantitatively to convert chemical or biochemical concentrations or activities of interest into electrical signals. These systems can be grouped into four major categories: reflection techniques; surface plasmon resonance; fibre optic techniques and integrated optic devices. Reflection techniques include ellipsometry, multiple integral reflection spectroscopy, and fluorescent capillary fill devices. Fibre-optic techniques include evanescent field fluorescence, optical fibre capillary tube, and fibre optic fluorescence sensors. Integrated optic devices include planer evanescent field fluorescence, input grading coupler immunosensor, Mach-Zehnder interferometer, Hartman interferometer and difference interferometer sensors. These examples of optical immunosensors are described in general in a review article by G. A. Robins (Advances in Biosensors), Vol. 1, pp. 229–256, 1991. More specific description of these devices are found for example in U.S. Pat. Nos. 4,810,658; 4,978,503; 5,186,897; R. A. Brady et al. (Phil. Trans. R. Soc. Land. B 316, 143–160, 1987) and G. A. Robinson et al. (in Sensors and Actuators, Elsevier, 1992).

In one embodiment of the present invention, myosin light chain is detected in a sample of blood, serum or plasma, using the monoclonal antibody of the present invention, in a device comprising a filter membrane or solid support with a detection section and a capture section. The detector section contains an antibody (a detector antibody), which will react with the myosin light chain. The detector antibody is reversibly immobilized onto the solid support and will migrate with the sample, when in use. It is preferred that the detector antibody is labelled, for example with a radionucleotide, an enzyme, a fluorescent moiety, luminescent moiety or a coloured label such as those described in the prior art, and discussed above. The capture section comprises a capture antibody, which is irreversibly immobilized onto the solid support. The antibodies, capture and detector antibody, and the necessary reagents are immobilized onto the solid support using standard art recognized techniques, as disclosed in the flow-through type immunoassay devices discussed previously. In general, the antibodies are absorbed onto the solid supports as a result of hydrophobic interactions between non-polar protein substructures and non-polar support matrix material.

According to this embodiment of the present invention, if the myosin light chain is present in the blood, it will react with the detector antibody in the detector section and will migrate on the filter membrane towards the capture section where the analyte will further bind with the capture antibody. Thus, the myosin light chain will be sandwiched between the capture antibody and the detector antibody, which contains a suitable label.

In this example of the present invention, if the detector antibody is labelled with a coloured label or an enzyme which will produce a coloured label, the patient's blood would first require centrifugation or some pre-filtering in order to remove the red blood cells so that the colour of the red blood cells will not interfere with the coloured labels. If radioactive labels or florescent labels are to be used, a pre-filtration or centrifugation step may not be required. In this embodiment, the monoclonal antibody of the present invention can be either the capture antibody or the detector antibody. In one embodiment, the monoclonal antibody of the present invention is a capture antibody. The detector antibody can be other cardiac specific myosin light chain monoclonal antibodies, monoclonal antibodies reactive to other isoforms of myosin light chain, or polyclonal antimyosin light chain antibodies. Either chicken, rabbit, goat or mouse polyclonal antibodies can be used. Many such antibodies are known and can be prepared and labelled by known methods.

This immunoassay system is generally described in U.S. Pat. No. 5,290,678. The antibody of this invention is particularly useful in this system because of its high affinity for cardiac myosin light chain.

The following detailed examples will further illustrate the invention, which are not to be construed as limiting.

EXAMPLES

Example 1

Preparation of Antigen

The peptide, B39 (residues 34 to 44), with branching polylysine core were synthesized by the Biotechnology Service Centre, Toronto, Ontario, Canada using the Tam method referred to above. Residue 34 to 44 was chosen by computer program analysis, which predicts immunogenic areas within a molecule. FIG. 1 shows the octameric structure of the branched peptides and the peptide sequence of B39 corresponding to cardiac MLC-1 is provided in Table 1. The lyophilized peptide was kept with a desiccant at −20° C. Immediately prior to use, the required amount of peptide was weighed and dissolved in 10 mM phosphate buffered saline (PBS), pH 7.4. The final concentration of the peptide was about 2 mg/ml.

TABLE 1

Synthetic Peptide Sequence

| Peptides | Peptide Sequence | Position of Peptide |
|---|---|---|
| B39 | Glu—Val—Glu—Phe—Asp—Ala—Ser—Lys—Ile—Lys—Ile (SEQ ID NO:1) | 34–44 |

Example 2

Preparation of Monoclonal Antibody

The monoclonal antibody of the present invention was produced by the polyethylene glycol (PEG) mediated cell fusion method.

i) Preparation of immunocytes

Balb/c mice, a strain with H-2$^d$ haplotype from Charles River Canada, St. Constant, Quebec, Canada, female, 7–9 week old, were immunized with the branched peptide emulsified in an equal volume of either Freund's complete adjuvant (FCA) for the first injection and then in Freund's incomplete adjuvant (FIA) for subsequent injections at two week intervals with 100 µg of peptide. Immunized mice were sacrificed 3–4 days after the final immunization, given either intravenously and/or intraperitoneally, in phosphate buffered saline buffer (PBS), pH 7.4.

ii) Preparation of myeloma cells

Sp2/0-Ag 14 (Sp2/0) mouse myeloma cells were obtained from ATCC (ATCC CRL-1581).

iii) Preparation of Hybridoma

Spleen cells from the mice immunized with the branched peptide and the Sp2/0 cells were fused in the presence of 42% PEG according to the method described by Fuller, S. A., Takahashi, M., and Hurrell, J. G. R. (Preparation of Monoclonal Antibodies: In: Ausubel F, Brent B, Kingston R., et. al., eds. Current Protocols in Molecular Biology. New York: Greene Publishing Associates, 1987: Unit 11). The resulting fused cells were suspended in the HAT selection medium and plated onto five 96-well plates which were pre-seeded with feeder cells, PEC (peritoneal exudate cells), as described by Fuller et al. (see above reference). Fresh HAT medium was added on day 7 post-fusion, and on day 9, 50% of the culture medium was removed and replaced with fresh HAT medium.

iv) Screening of MLC-1 specific antibody-secreting hybridomas

The initial screening of hybridoma cultures was carried out using solid-phase ELISA. Confluent hybridoma culture supernatants were added to 96-well microtitre plates coated with either the branched peptide or myosin light chin, purified from human cardiac muscle. Specifically, the antigen was immobilized directly onto the plastic surface of 96-well Immunolon-4, flat-bottom microtiter plates (Dynatech Labs, Chantilly, Va.) by incubating overnight at 4° C. with 100 µl per well of protein solution at 1 µg/ml in 100 mM carbonate buffer, pH 9.6. The excess binding sites were blocked by bovine serum albumin (BSA) in phosphate buffered saline (PBS), pH 7.2. After washing the plate with PBS containing 0.05% Tween 20, 100 μl of the culture supernatants containing the monoclonal antibodies were incubated with the immobilized antigen for 1 h at 37° C. After washing, peroxidase conjugated goat anti-mouse IgG (Jackson ImmunoResearch Lab, Inc., West Grove, Pa.) was added and incubated for 30 min. at 37° C. After the last washing, orthophenylene diamine (OPD) (Sigma Chemicals, St. Louis, Mo.), 10 mg in 12.5 ml 0.1 mol/L citrate buffer, pH 5.0, containing 125 μl 3% $H_2SO_4$ was added and optical density was read at $490_{nm}$. Positive cultures were fed with fresh medium and 24 hours later, ELISA screening was repeated, as described above. Cultures giving the same or greater OD signal to the first ELISA were transferred onto 24-well culture plates pre-seeded with feeder cells, as described above.

The cultures positive in both the peptide-plate and the MLC-plate were subjected to cloning by the limiting dilution method, as described by Fuller et al. (see above reference). Solid-phase ELISA screening of the secondary hybridoma cultures were repeated using both the MLC- and the peptide-plates. Cultures positive in both plates were expanded onto 24-well culture plates. When hybridomas reached confluency, the culture supernatants were examined using the BIAcore system (Pharmacia Biosensor AB, Uppsala, Sweden) to evaluate whether or not the antibody binds the antigen, i.e. myosin light chain in solution and to determine the profile of antigen binding kinetics. The BIAcore system uses surface plasmon resonance, which detects changes in optical properties at the surface of a thin gold film on a glass support. Detailed theoretical background and procedures are described by R. Karlsson, et. al. (J. Immunol. Methods, 145, 229, 1991).

Monoclonal antibodies at a constant concentration of 30 μg/ml in 10 mM Hepes, 0.15M NaCl, 3.4 mM ethylenediaminetetraacetic acid disodium salt, 0.05% surfactant 20 (HBS, pH 7.4) were allowed to interact with sensor surfaces on which rabbit anti-mouse $IgG_{Fc}$ (obtained from Jackson ImmunoResearch Lab, Inc., West Grove, Pa.) had been immobilized. The antigen, myosin light chain, at concentrations ranging from 1.25 μg/ml to 20 μg/ml, was allowed to interact with the bound monoclonal antibodies. The runs were performed at 25° C., at a flow rate of 5 μl/min during 6 min. (30 μl injection). After the run, the surface was regenerated by injecting a 1M formic acid solution during 1 min. (5 μl injection). The BIAcore system analysis confirms not only the myosin light chain-specificity of the antibody but also the capability of the same to capture myosin light chain in solution. The latter can be a critical confirmation of the usefulness of the antibody. Often clones screened and isolated by solid-phase ELISA fail to recognize the antigen in solution. Such antibodies can not be utilized in diagnostic immunoassay systems.

A selected culture, based on the results obtained by solid-phase ELISA and BIAcore analysis, was further subjected to cloning until culture stability and clonality were obtained. This hybridoma cell line was deposited with the American Type Culture Collection on Aug. 25, 1994 under Accession Number HB 11709.

v) Production of monoclonal antibody

The myosin light chain specific monoclonal antibody was produced either using a bioreactor or from ascites. Ascites were produced in Balb/c mice previously treated with 0.5 ml of pristane by injecting intraperitoneally with $1-5\times10^6$ hybridoma cells in 0.5 ml PBS, pH 7.4. Approximately 2 weeks later, ascites were collected. The monoclonal antibody, either from bioreactor harvest or ascites was purified on affinity column (Protein A, Protein G, AVID AL), using known procedures. The purified monoclonal antibody was used for immunochemical studies.

Example 3

Specificity of the Monoclonal Antibody Against HVMLC i) Solid-phase ELISA

A conventional solid-phase ELISA was used to determine the specificity of the monoclonal antibody of the present invention. All of the purified cardiac and skeletal isoforms of MLCs, as well as the branched peptide, were mobilized directly onto the plastic surface of a flat-bottom microtitre plate (Dynatech Labs, Chantilly, Va.) by incubating overnight at 4° C. with 100 μl per well of protein or peptide solution at 5 μg/ml in 100 mM carbonate buffer, pH 9.6. The excess binding sites were blocked by bovine serum albumin (BSA) in PBS, pH 7.2 overnight at 4° C. for MLC plates and the peptide plates were blocked with 5% (w/v) skim milk in PBS, pH 7.2 overnight at room temperature. After washing the plates with PBS containing 0.05% Tween 20, 100 μl of the monoclonal antibody at 10 μg/ml was added for 1 h at 37° C. After rinsing the plates, peroxidase conjugated goat anti-mouse IgG (Jackson ImmunoResearch Lab, Inc., West Grove, Pa.) was added and incubated for 30 min. at 37° C. After the last washing of the plates, orthophenylene diamine (OPD, 10 mg in 12.5 ml 0.1 mol/L citrate buffer, pH 5.0, containing 125 μl of 3% $H_2SO_4$) was added and optical density was read at $490_{nm}$.

As summarized in Table 2, the 39-15 monoclonal antibody reacted equally well with both the synthetic peptide and the native protein. Cross-reactivity of the monoclonal antibody with skeletal isoforms was apparent. The monoclonal antibody did not react with either human IgG or human serum albumin.

As a practical matter, cross reactivity between the antibody of this invention and both cardiac myosin light chain and skeletal myosin light chain is not a problem with patients to whom the fast format technique is applicable. Skeletal myosin light chain normally appears only when there is some injury to skeletal support muscle, as for example in surgery or broken bones. Most patients presenting with chest pain have not been subjected to such skeletal trauma. Those that have been so subjected will be readily apparent to the technician or clinician and the fast format procedure will not be employed. The essence of this invention is the high affinity of the monoclonal antibody for cardiac myosin light chain. This is the property which makes it so valuable for rapid format procedures. The high affinity of this particular antibody coupled with its reactivity with cardiac myosin light chain is surprising since previously described antibodies which are specific for cardiac myosin light chain with no cross reactivity with the skeletal variety did not have high affinity for cardiac myosin light chain and were not useful in fast format techniques.

TABLE 2

| Solid-phase ELISA Results | |
|---|---|
| Isotype | 39-15* IgG1,k |
| Cardiac | |
| MLC1 | ++++ |
| MLC2 | +++ |
| Slow Skeletal | |
| MLC1 | ++++ |
| MLC2 | − |
| Fast Skeletal | |

TABLE 2-continued

Solid-phase ELISA Results

| Isotype | 39-15*<br>IgG1,k |
|---|---|
| MLC1 | +++ |
| MLC2 | ++ |
| MLC3 | + |
| Synthetic Peptide B39 | ++++ |
| Human IgG | − |
| Human Serum Albumin | − |

*Hybridomal Cell Line

| $OD_{490nm}$ | − | <0.09 |
| | + | 0.1–0.5 |
| | ++ | 0.5–1.0 |
| | +++ | 1.0–1.5 |
| | ++++ | >1.5 | ii) Sandwich ELISA

The 39-15 monoclonal antibody was immobilized onto the plastic surface, as capture antibody, as described in the solid-phase ELISA. Cardiac MLC-1 was measured at concentrations ranging from 0.1 to 100 ng/ml in PBS, pH 7.2 with 0.25% albumin, 0.05% Tween 20 and 0.05% thimerosal. The standard MLC-1 solutions were incubated for 30 min at room temperature on a shaker. After rinsing the plate with TTBS (PBS containing 0.05% Tween, pH 7.2), peroxidase conjugated affinity purified chicken anti-MLC-1 was added and incubated for 30 min at room temperature on a shaker. This is a polyclonal antibody prepared from myosin light chain-immunized chickens, prepared using standard procedures. IgG is purified from egg yolk using dextran sulphate precipitation followed by affinity purification using mobilized cardiac myosin light chain 1. After washing the plate, the bound enzyme activity was measured by addition of OPD substrate solution, as described above. After 10 min incubation in the dark at room temperature, the reaction was stopped with 2M $H_2SO_4$ and the results were read at $A_{490nm}$.

Figure 2:
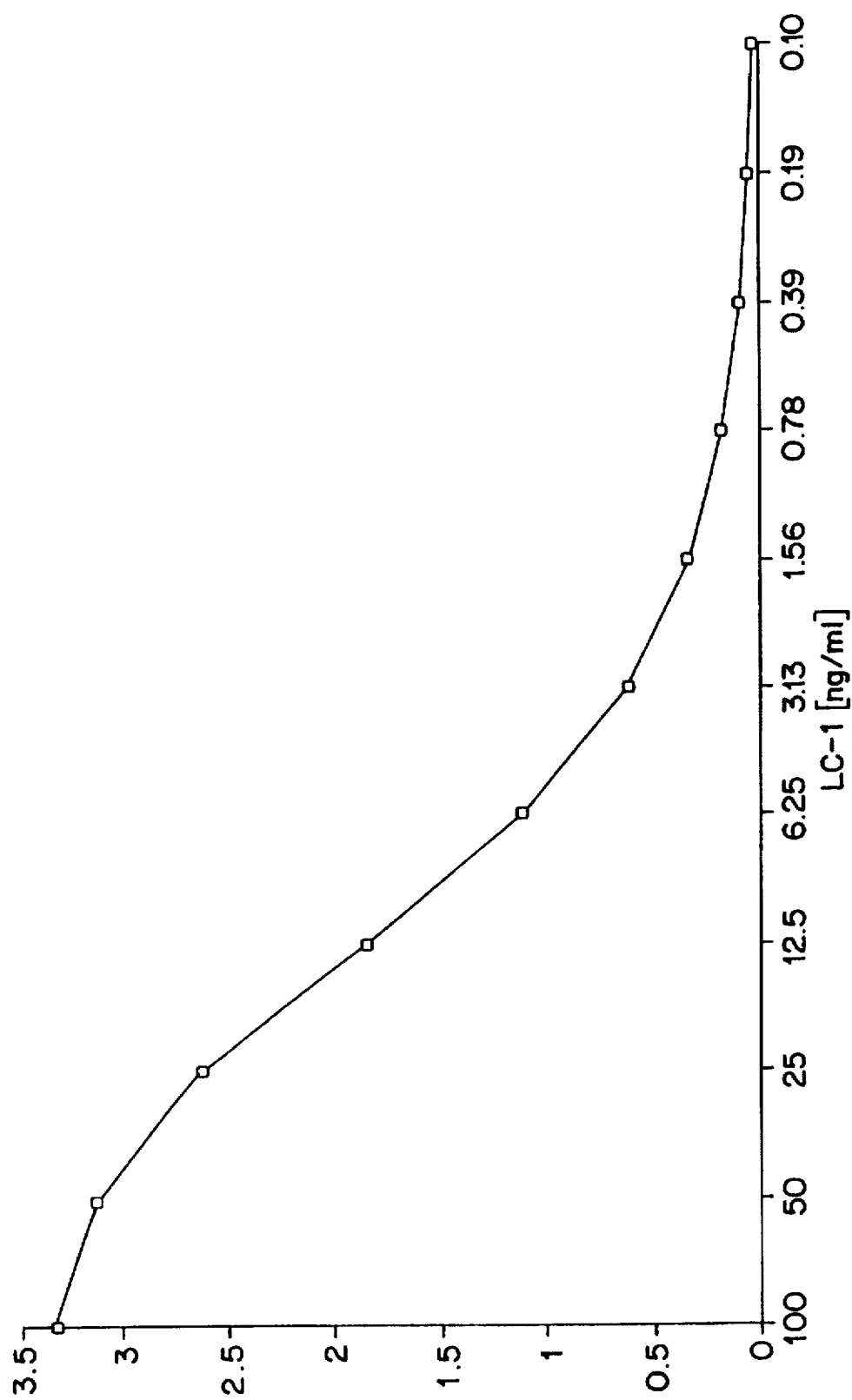
FIG. 2 shows the results of a sandwich assay of HVMLC-1, wherein MAb 39-15 was used as the capture antibody and affinity purified chicken anti-MLC-1 was used as the detector antibody.

As shown in FIG. 2, using monoclonal 39-15 as capture antibody, the minimum detectable level of cMLC-1 in the sandwich ELISA was 0.5 ng/ml.

Example 4

Physico-chemical Properties of the Monoclonal Antibody Produced by Hybridoma Cell Line 39-15

The physico-chemical properties of the monoclonal antibody produced by hybridoma cell line 39-15 (Monoclonal 39-15) are summarized in the Table 3.

TABLE 3

Physico-chemical Properties of Monoclonal 39-15

| Subclass | IgG1,k |
|---|---|
| Western Blot | Myosin Specific |
| pI Value | 6.9 |
| $Ka(M^{-1})$ | $5.0 \times 10^8$ |
| $Kd(M)$ | $2.0 \times 10^{-9}$ | i) Antibody Class and Subclass Determination

Antibody class and subclass determination was performed by ELISA using a commercial kit (Bio-Rad, Hercules, Calif., Cat no. 172-2055), using the method described by the manufacture. The monoclonal 39-15 is a IgG1, k.

ii) Isoelectric Point

Isoelectric focusing on the monoclonal 39-15 was performed using the Bio-Rad Mini IEF cell (BioRad, Hercules, Calif. Cat. no. 1702975) following the instructions provided by the manufacturer. The pI value of 39-15 was estimated to be 6.9.

iii) Affinity constants

Kinetic and affinity constants for the interaction between monoclonal 39-15 and cardiac MLC-1 was determined using the BIAcore system (Pharmacia Biosensor AB, Uppsala, Sweden). The system uses surface plasmon resonance, which detects changes in optical properties at the surface of a thin gold film on a glass support. Studies were performed based on the detailed description by R. Karlsson, et al. (J Immunol Methods, 145, 229, 1991).

Kinetic runs were performed as follows: The monoclonal antibody at a constant concentration of 30 µg/ml in 10 mM Hepes, 0.15M NaCl, 3.4 mM ethylenediaminetetraacetic acid disodium salt, 0.05% surfactant 20 (HBS, pH 7.4) were allowed to interact with sensor surfaces on which rabbit anti-mouse $IgG_{Fc}$ (Jackson ImmunoResearch Lab, Inc.) had been immobilized. The antigen, cardiac myosin light chain-1, at concentrations ranging from 1.25 µg/ml to 20 µg/ml, was allowed to interact with the bound monoclonal antibody. The runs were performed at 25° C., at a flow rate of 5 µl/min during 6 min. (30 µl injection), taking a total of 24 report points. After injection of the antigen was complete, dissociation of the antigen from the antibody was monitored by taking a total of 18 report points. After the run, the surface was regenerated by injecting a 1M formic acid solution during 1 min. (5 µl injection). The instrument software produces a table of $dR_A/dt$ and $R_A$ values that can be directly used in a plotting program (Microsoft Excel).

As shown in Table 3, the $Ka(M^{-1})$ of monoclonal 39-15 is $5.0 \times 10^8$ while the $Kd(M)$ is $2.0 \times 10^{-9}$. It is commonly observed by various users of BIAcore that the log affinity constant value estimated on BIAcore appear 1.0 lower than the actual value. Monoclonal 39-15 shows a very high affinity for the antigen, cardiac MLC-1.

iv) Antigenic specificity determined by western blot

Western blot was performed using the Bio-Rad apparatus (Mini Trans Blot Cell, no. 170-3930) using the manufacturer's reagents and instruction. Monoclonal 39-15 shows specificity for cardiac MLC-1 and no binding to myosin heavy chain or MLC-2 blotted onto nitrocellulose membrane. Thus, using Western blot for antigenic specificity determination, monoclonal 39-15 appears to be myosin light chain specific.

Example 5

Detection of Myosin Light Chain in a Biological Sample

In this example, the monoclonal antibody produced from hybridoma cell line 39-15 was used as a capture antibody in a flow through assay system, based on the double antibody sandwich assay.

A sample of a patient's serum (50 µl to 150 µl) was added to the assay system through a sample opening, which was in fluid communication with a reagent pad containing a labelled detector antibody. The detector antibody was a polyclonal antibody prepared from myosin light chain-immunized chickens, as described in a preceding example. If the sample size was small a carrier fluid was added after the application of the sample. The carrier fluid can be any buffer solution; for example phosphate buffer, saline, Tris-HCl or water. If the sample contained myosin light chain it will bind to the detector antibody in the reagent pad. The detector antibody being reversibly immobilized and thus migrated with the sample. The sample continued to flow from the reagent pad onto a filter membrane, onto which the monoclonal antibody of the present invention was irreversible immobilized (capture antibody). Labelled detector antibody-myosin light chain complex, if present will bind to the capture antibody on the filter membrane. The presence of the analyte which has been labelled with the labelled detector antibody was thus positioned at the location of the capture antibody, which generally coincides in position to a display window in the assay system.

All references cited herein are specifically incorporated by reference.

Although the disclosure describes and illustrates preferred embodiments of the invention, it is to be understood that the invention is not limited to these particular embodiments. Many variations and modifications will now occur to those skilled in the art. For a definition of the invention, reference is made to the appended claims.

We claim:

1. A hybridoma cell line 39-15, deposited with American Type Culture Collection under Accession Number HB 11709.

2. A monoclonal antibody produced from hybridoma cell line 39-15, deposited with American Type Culture Collection under Accession Number HB 11709.

3. A method of detecting cardiac myosin light chain 1 in a sample using a monoclonal antibody produced from hybridoma cell line 39-15, deposited with American Type Culture Collection under Accession Number HB 11709, which comprises contacting the sample with the monoclonal antibody to effect an immunoreaction between the cardiac myosin light chain-1 in the sample and the monoclonal antibody; and detecting the immunoreaction.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( v ) FRAGMENT TYPE:

( x i ) SEQUENCE DESCRIPTION: SEQ ID NO:1:

```
Glu  Val  Glu  Phe  Asp  Ala  Ser  Lys  Ile  Lys  Ile
 1              5                        10
```